US012508164B2

(12) United States Patent
Jones

(10) Patent No.: US 12,508,164 B2
(45) Date of Patent: Dec. 30, 2025

(54) AIR COLLIDER REPELLENT GOGGLES

(71) Applicant: Brian Alan Jones, Eatonville, WA (US)

(72) Inventor: Brian Alan Jones, Eatonville, WA (US)

( * ) Notice: Subject to any disclaimer, the term of this patent is extended or adjusted under 35 U.S.C. 154(b) by 0 days.

(21) Appl. No.: 17/803,190

(22) Filed: Jun. 30, 2023

(65) Prior Publication Data

US 2025/0000704 A1 Jan. 2, 2025

Related U.S. Application Data

(60) Provisional application No. 63/337,132, filed on May 1, 2022.

(51) Int. Cl.
*A61F 9/00* (2006.01)
*A61F 9/02* (2006.01)

(52) U.S. Cl.
CPC .............. *A61F 9/028* (2013.01); *A61F 9/029* (2013.01)

(58) Field of Classification Search
CPC ............. A61F 9/04; A61F 9/028; A61F 9/029
See application file for complete search history.

(56) References Cited

U.S. PATENT DOCUMENTS

| | | | | |
|---|---|---|---|---|
| 5,033,128 | A * | 7/1991 | Torres | A62B 18/00 2/427 |
| 6,772,448 | B1 * | 8/2004 | Hockaday | A61F 9/028 2/435 |
| 2011/0258758 | A1 * | 10/2011 | Renaud-Goud | A61F 9/027 2/427 |
| 2013/0050633 | A1 * | 2/2013 | Kikuyama | A61F 9/02 351/178 |
| 2013/0340152 | A1 * | 12/2013 | Cunningham | A61F 9/028 2/431 |
| 2015/0374550 | A1 * | 12/2015 | Saylor | A61F 9/028 2/436 |
| 2018/0279870 | A1 * | 10/2018 | Walsh | A61B 3/102 |
| 2020/0297538 | A1 * | 9/2020 | Xie | A61F 9/027 |
| 2020/0346050 | A1 * | 11/2020 | Xie | A62B 23/02 |
| 2020/0348539 | A1 * | 11/2020 | Xie | A61F 9/028 |
| 2022/0026746 | A1 * | 1/2022 | Lewis | G02C 11/08 |
| 2022/0225705 | A1 * | 7/2022 | Van Straten | A41D 13/1161 |
| 2023/0363951 | A1 * | 11/2023 | Cooper | A61F 9/028 |
| 2024/0215815 | A1 * | 7/2024 | Walsh | A61B 3/102 |

* cited by examiner

*Primary Examiner* — Richale L Quinn

(57) ABSTRACT

Eye protection goggles specifically designed to in a 'hands free' manner, eliminate airborne particulate materials, liquids or fluids from contacting the outer surface of the lens, as well as eliminating any fogging of the inner surface of the viewing lens.

1 Claim, 8 Drawing Sheets

AIR COLLIDER REPELLENT GOGGLES

BACKGROUND OF THE INVENTION

Figure 1:
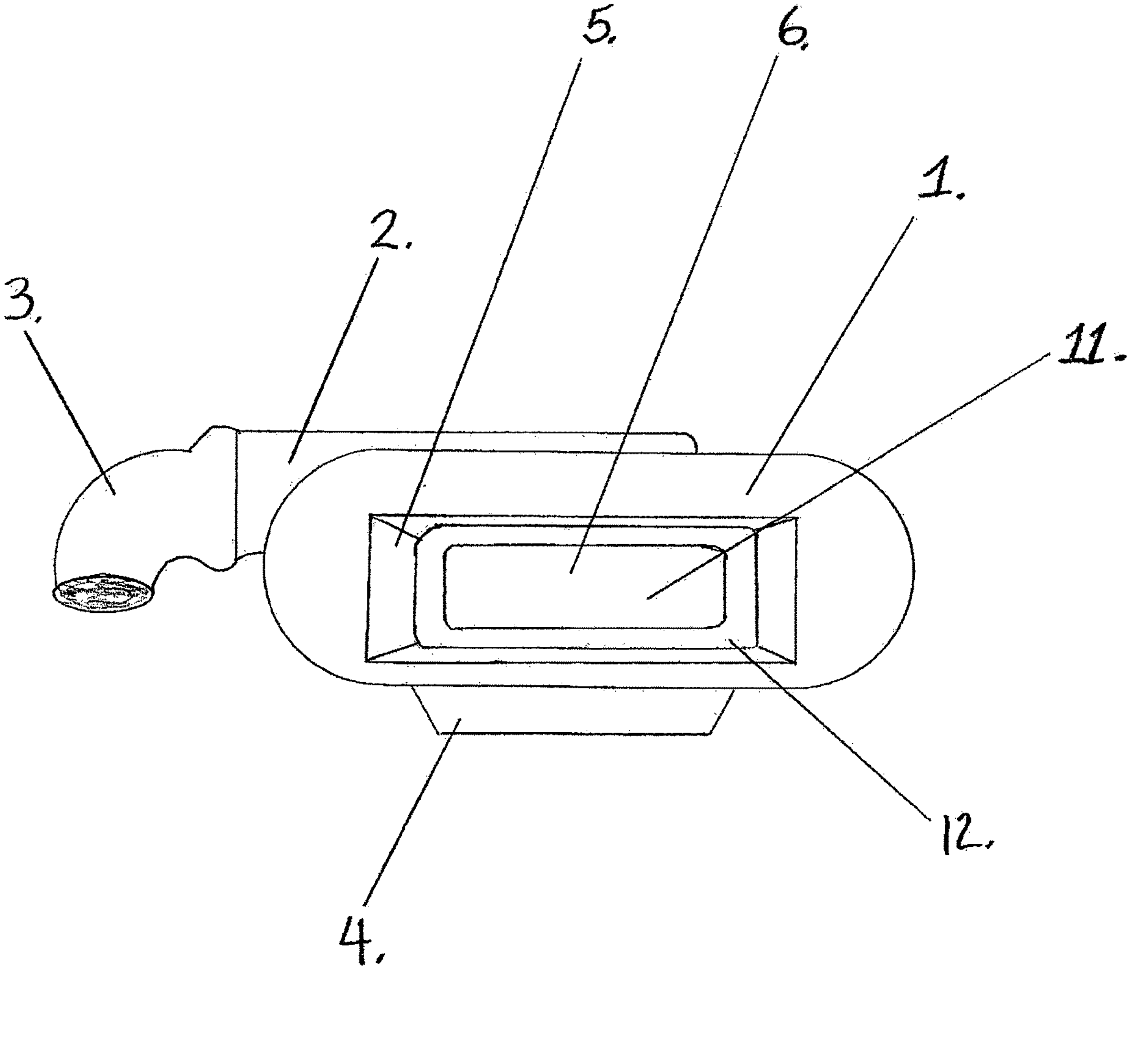

The initial goal of conceiving and creating the A.C.R.G. device was to realize a powerful and completely effective solution for protecting the eyes of painters operating the widely used airless paint sprayers designed for residential and commercial interior and exterior painting, where quite often the significant over-spray or discharge of sprayed material lands directly upon the eyeballs of the painter. In the case of this type of paint application, standard eye protective goggles and see-through face shields do not work, due to the fact that the excess paint discharge coats the outside of the clear lenses or shields to such degrees that vision is severely compromised, quite often almost immediately in the spraying process. In many cases, clear vision is required to see the materials in close detail as they are being applied to the surfaces, so the operator really suffers personally relying upon their own tear ducts and blinking their eyes, in an attempt to wash clear the materials landing directly upon them.

To this very day, all the painters I have spoken with state that they have no viable solution or option to remedy this unfortunate aspect of this profession, and actually are simply enduring this severe assault of their eyes in order to get the job done. During the years of this process I have invested in conceiving, experimenting, and building a strongly successful device to remedy the plight of the painters in this massive and highly common industry, I have come to realize that the A.C.R.G. device could also be used in many additional circumstances of great consequence to protect eyes from airborne particulate materials, both wet and dry. Another key and critical solution realized by the A.C.R.G.'s highly effective built-in Forced-Air Defogger and Dehumidification system, is that it completely eliminates the fogging of the internal side of the Viewing Lens, which is Also prevalent and dramatic impediment inherent with most enclosed eye protection goggles, caused from the moisture produced by perspiration or in some cases, breath moisture.

SUMMARY OF THE INVENTION

The A.C.R.G. device utilizes a high velocity of forced air supplied to the device through a single over-the-shoulder hose, delivered by a variety of external types of pre-existing and readily available equipment, such as shop vacuum cleaners with exhaust side connection, leaf blowers, hand-held, as well as back-pack mounted. Another option for the forced air supply is a stationary blower unit. These forced air supply devices can be powered by corded 120 Volts AC, as well as utilizing the more portable and unencumbered cordless battery and gasoline powered versions of forced air blower devices. This high volume and pressure of the air is directed through internal chambers and restricted channels exiting on both sides of and across the exterior surface of the clear lens of the goggles. Inside the calibrated open-faced viewing chamber in front of the outside of the lens, the air is meeting in the middle in a head on collision and subsequent explosive omnidirectional expansion of the invisible high velocity air exiting through the forward tapered down opening, thus generating an invisible repellent force field, rejecting all airborne and discharged material from entering the viewing chamber or getting anywhere near the outside of the lens. A very small amount of this forced air is directed internally, directed downward across the entire surface of the inside of the viewing lens and exhausting out of the inside of the goggles across the bottom of the lens, and in so doing, eliminates any and all fog from forming on the inside of the lens, as well as expelling any additional moisture inside the inside of the main goggle housing out through this exhaust port.

LIST AND DESCRIPTION OF THE SEVERAL VIEWS OF THE DRAWING

FIG. 1. Front View showing locations of these components:

(1) Main Housing, (2) Primary Air Duct, (3) 90 Degree Curved Air Inlet Connector (4) Face Connecting Section, (5) Tapered Air Outlet Housing, (6) Viewing Lens (11) View Chamber, (12) Restriction Rim for Forward Opening of (5)

Figure 2:
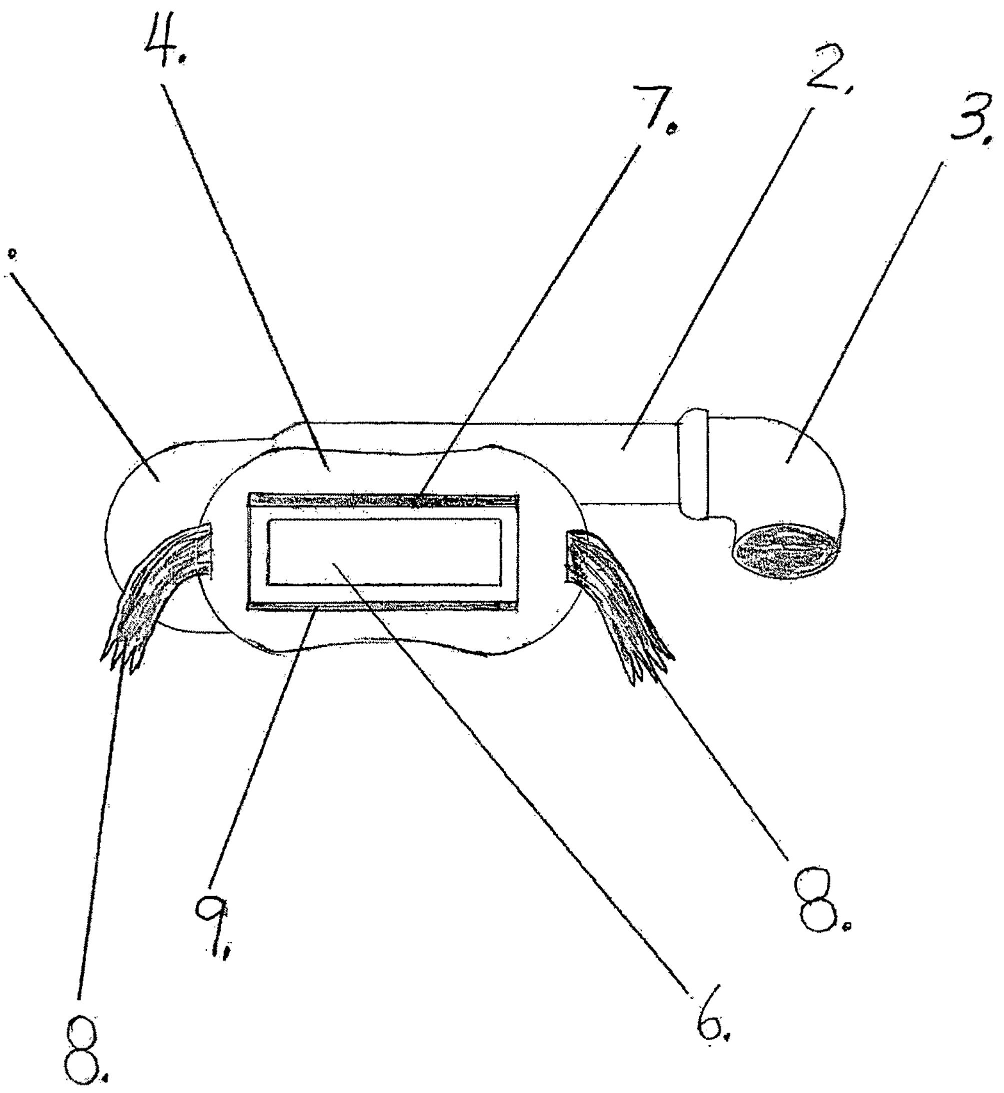
Figure 3:
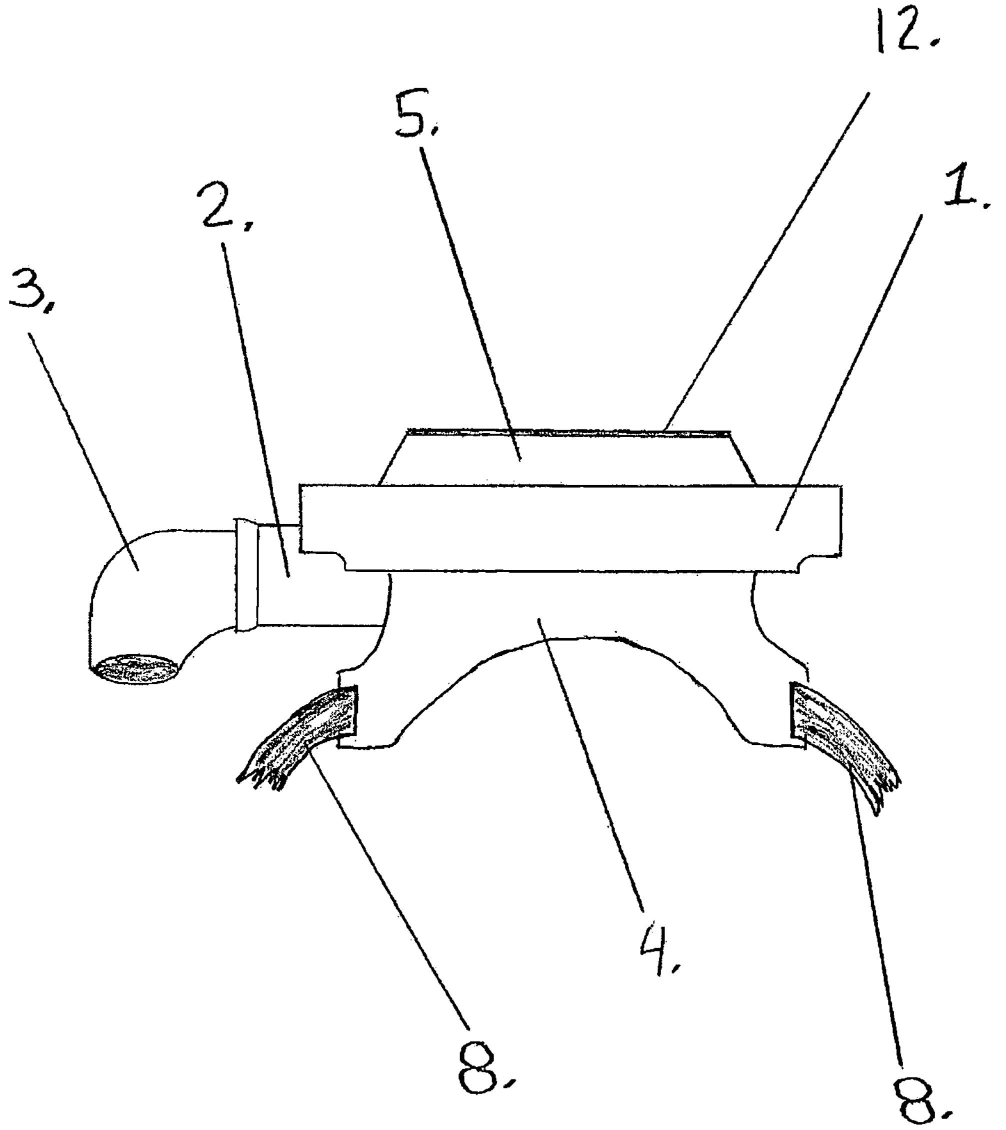

FIG. 2. Back View (face connecting side) showing locations of these components:

(1) Main Housing, (2) Primary Air Duct, (3) 90 Degree Curved Air Inlet Connector, (4) Face Connecting Section, (6) Viewing Lens, (7) Defogger Air-Charged Vent Strip, (8) Head Strap References (×2), (9) Defogger Air Outlet Vent Strip FIG. 3. Bottom View showing locations of these components:

(1) Main Housing, (2) Primary Air Duct, (3) 90 Degree Curved Air Inlet Connector (4) Face Connecting Section, (5) Tapered Air Outlet Housing, (8) Head Strap references (×2), (12) Restriction Rim for Forward Opening of (5)

Figure 4:
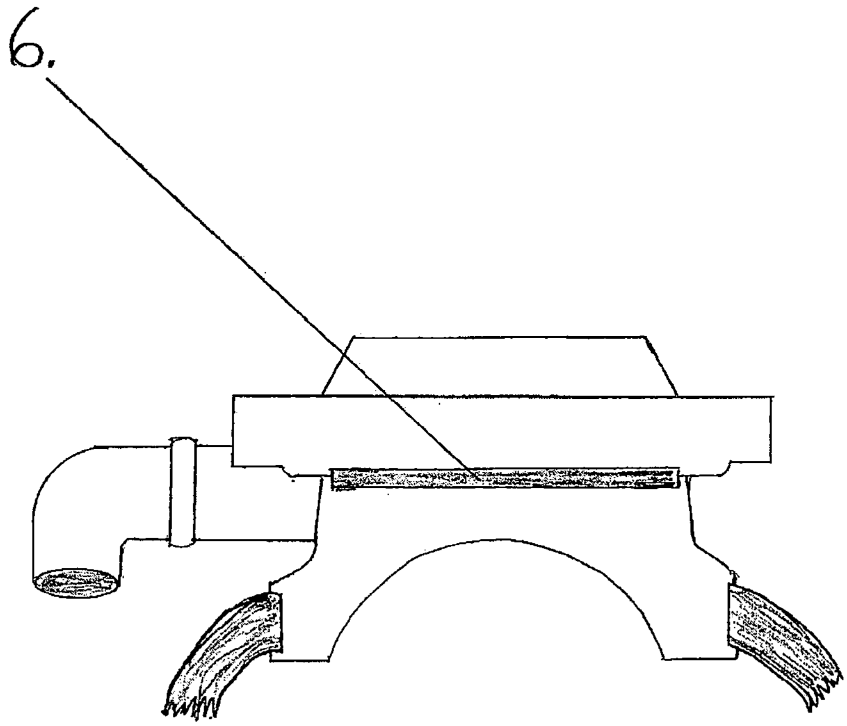

FIG. 4. Bottom View showing the location of the actual Viewing Lens:

(6) Viewing Lens

Figure 5:
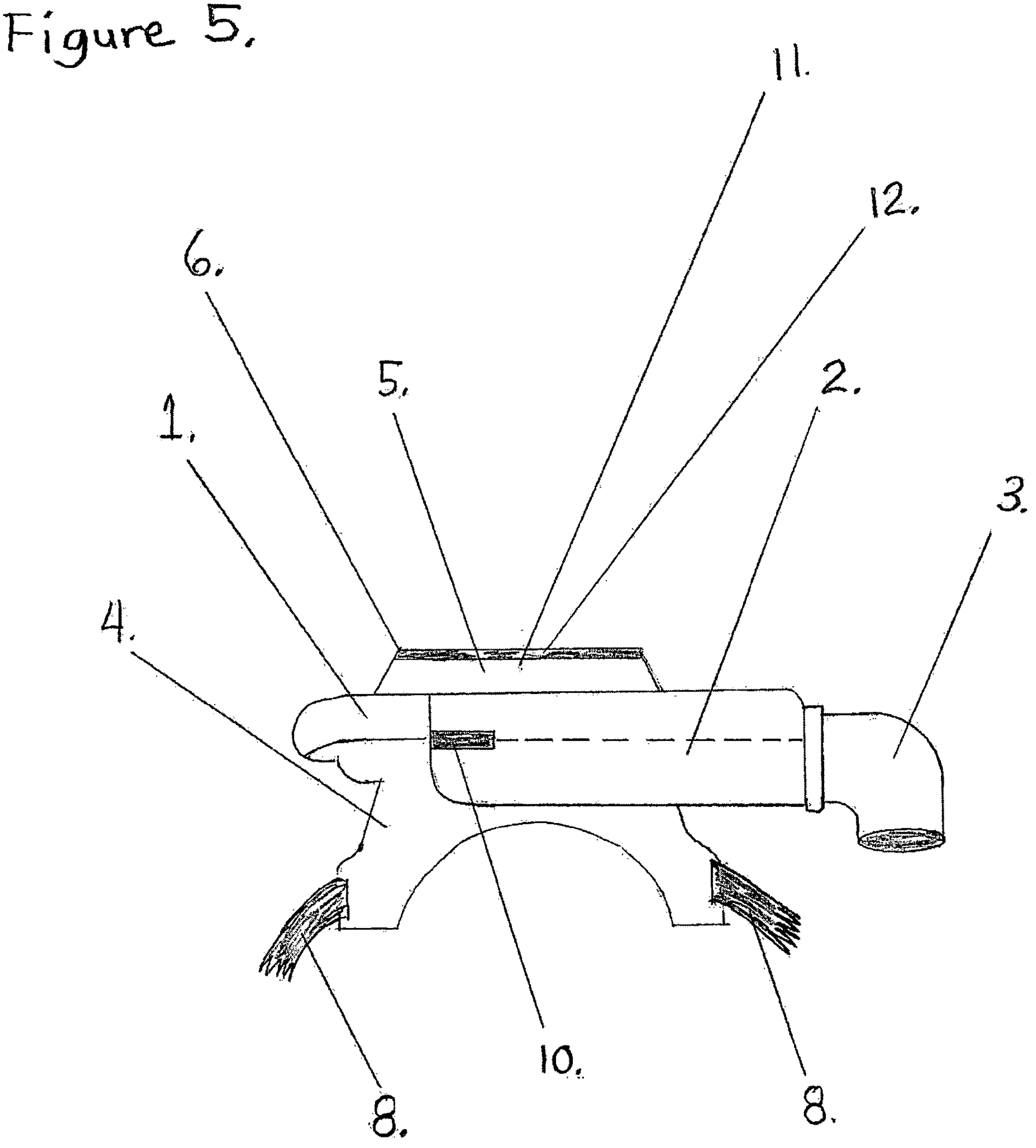

FIG. 5. Top View showing locations of these components:

(1) Main Housing, (2) Primary Air Duct, (3) 90 Degree Curved Air Inlet Connector (4) Face Connecting Section, (5) Tapered Air Outlet Housing, (6) Viewing Lens (8) Head Strap references (×2), (10) Internal Air Port Reference Between (1) and (2), (11) View Chamber, (12) Restriction Rim for Forward Opening of (5)

Figure 6:
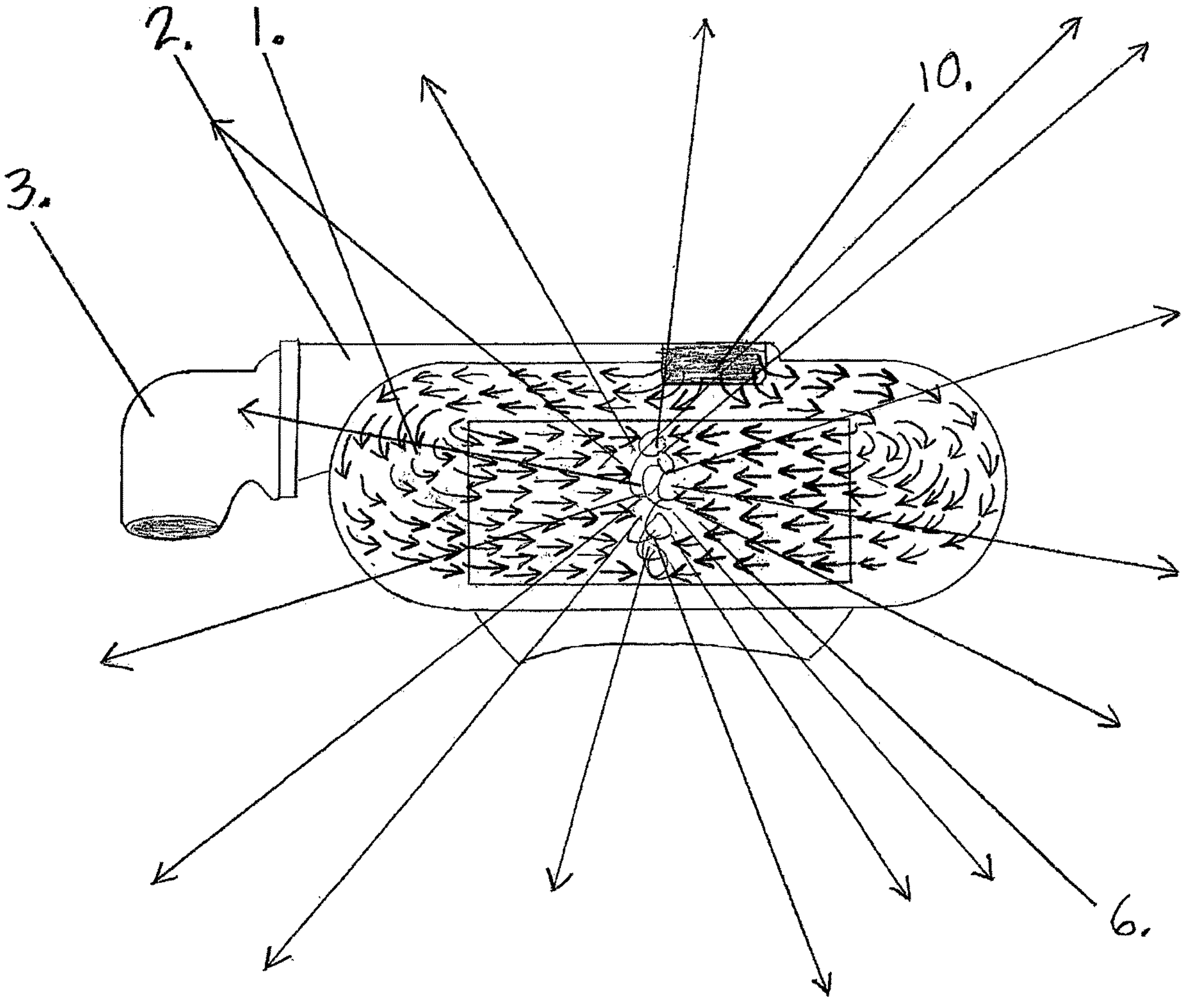

FIG. 6. Front View 'Opened' look at the inside the View Chamber showing directions of the forced air, and showing locations of these components:

(1) Main Housing, (2) Primary Air Duct, (3) 90 Degree Curved Air Inlet Connector, (6) Viewing Lens, (10) Internal Air Port Reference Between (1) and (2)

Figure 7:
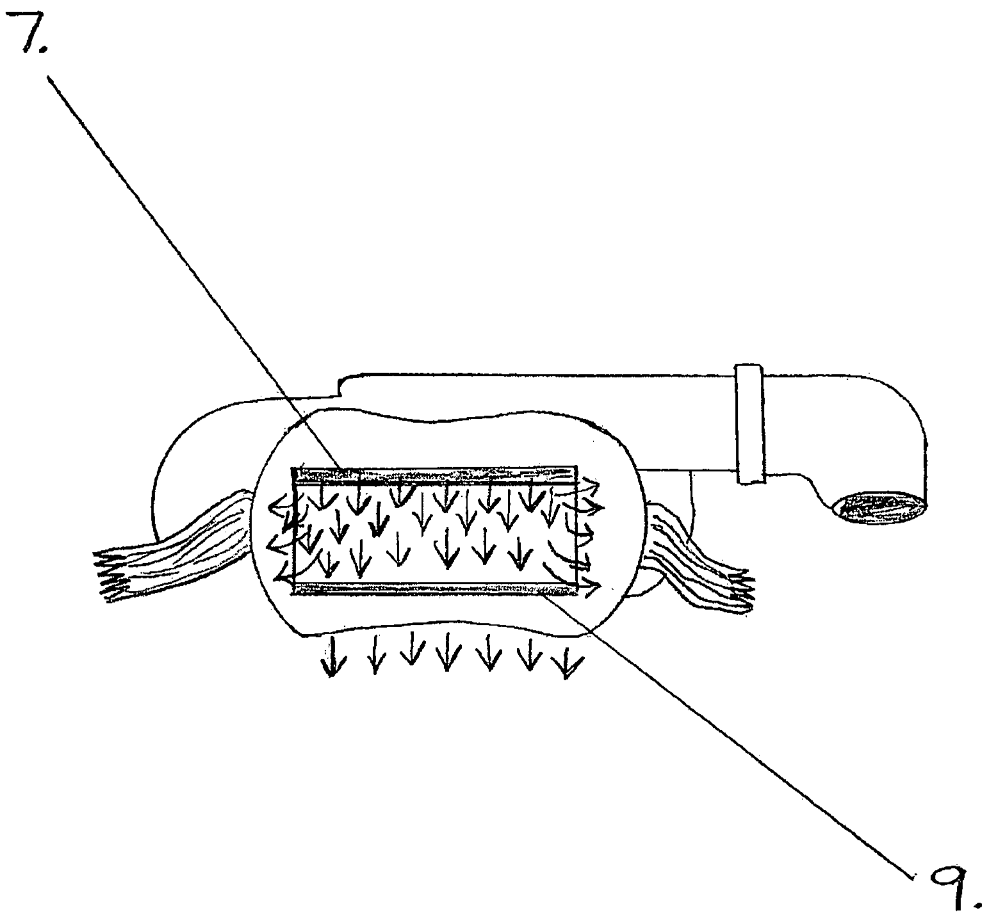

FIG. 7. Back View showing directions of the supplied air of the defogger system to the interior of the lens, as well as to the interior of the facial chamber fresh air circulation, and downward exhaust vent location:

(7) Defogger Air-Charged Vent Strip, (9) Defogger Air Outlet Vent Strip

Figure 8:
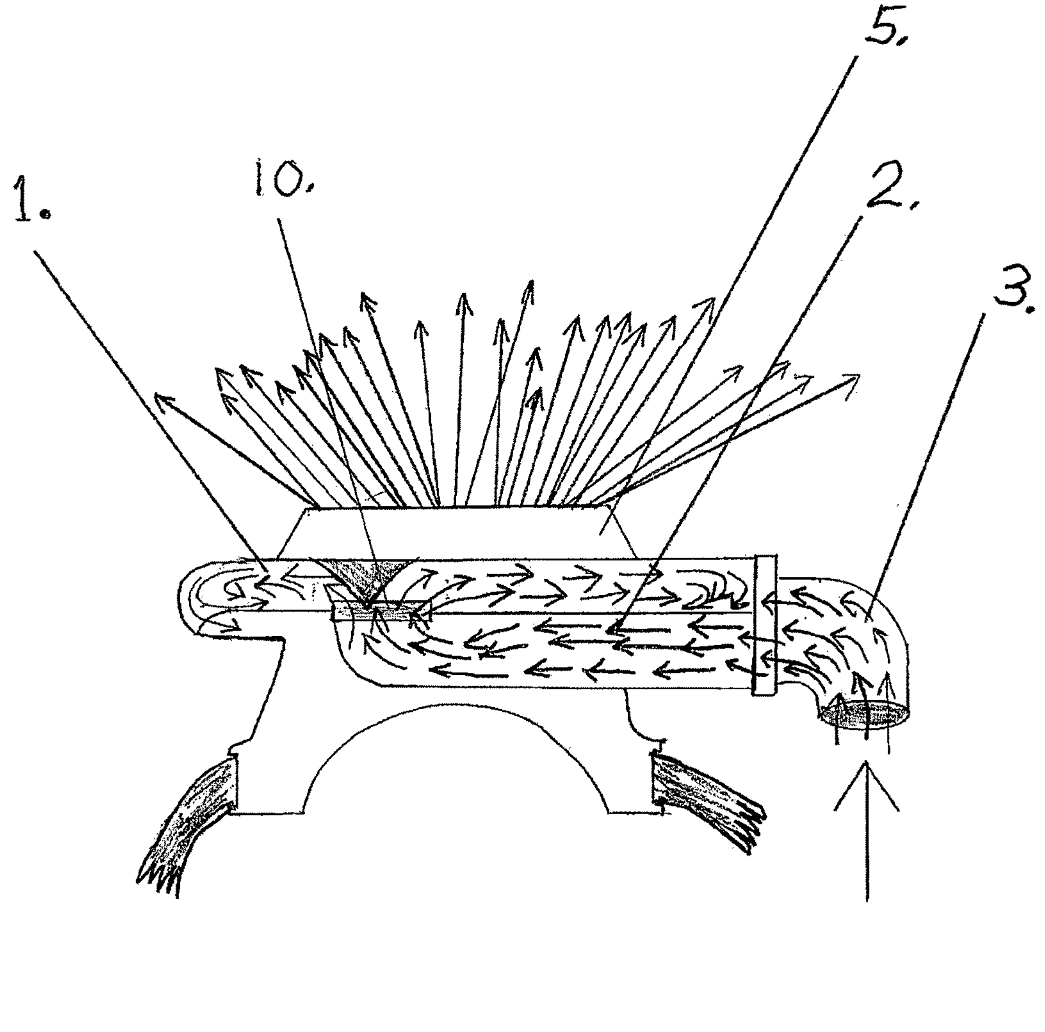

FIG. 8. Top View showing directions of the forced air through these components:

(1) Main Housing, (2) Primary Air Duct, (3) 90 Degree Curved Air Inlet Connector, (5) Tapered Air Outlet Housing, (10) Internal Air Port Reference Between (1) and (2)

COMPONENT NAMES AND COINCIDING NUMBERS (1) Main Housing (2) Primary Air Duct (3) 90 Degree Curved Air Inlet Connector (4) Face Connecting Section
(5) Tapered Air Outlet Housing
(6) Viewing Lens
(7) Defogger Air-Charged Vent Strip
(8) Head Strap references (×2)
(9) Defogger Air Outlet Vent Strip
(10) Internal Air Port Reference Between (1) and (2)
(11) View Chamber
(12) Restriction Rim for Forward Opening of (5)

Description of Forced Air Application and Function

The power and repelling force of the calibrated and directed air is introduced into the device as follows:

Pertaining to FIG. 8. (top view showing first phase of air travel):

A source of High-Volume and High-Velocity air is directed into (3) the 90 degree Air Inlet Connector, the air then travels at a Hard-Left 90 degree angle through (2) the Primary Air Duct, where at the other end of (2) takes another Hard-Right 90 degree turn and enters the top of (1) the Main Housing, where it is split in a calibrated way to evenly divide to Hard-Left and Hard-Right angles through sealed passages atop (11) the View Chamber. Also depicted within FIG. 8, is the Repellent Force Field of the omnidirectional air exiting (5) the Tapered Air Outlet Housing, represented in a generalized sense by the multiple straight-line arrows.

Pertaining to FIG. 6. (Front View of 'Opened' look at the inside of (11) the View Chamber showing the next phase of air travel) As the air travels through (10) the Internal Air Port Reference Between (1) and (2), it travels in opposite Left and Right directions through passage ways Over the top of and at this point is Separate From direct access to (6) the Viewing Lens. As the air reaches the Left and Right ends of the upper passage way of (1), it is directed downward through uniformly curved, calculated and calibrated restricted passages, the Left and Right channels of air is then directed head on towards each other sweeping across the forward (outer) surface of (6) the Viewing Lens, where upon head-on Collision meeting in the middle, the opposing forces of High-Volume and High-Velocity air violently Collides and explosively expands, creating an Invisible and Impenetrable 'Barrier' or 'Fence' outside of and in front of (6) 'that keeps all airborne material from coming anywhere near contacting or coating the outside of (6) the Viewing Lens.

Pertaining to FIG. 7. (Rear view of the inside of (4) the Face Connecting Section) Within (4), I have created extremely powerful Defogger and Dehumidification systems. A small percentage of the present and available Forced-Air as previously described, is directed downward through (7) the Defogger Air-Charged Vent Strip. Utilizing another calibrated restrictive attribute, the air sweeps downward across the rear (user's) side of the entire surface of (6), Completely Eliminating any perspiration caused moisture or fog from forming on this side of (6) the Viewing Lens. The amount of Forced-Air entering the inside of (4) is more than adequate to also expel through (9) the Defogger Air Outlet Vent Strip, ambient perspiration moisture present within the interior of (4).

What is claimed is:

1. A combination particle repeller, defogger and face protection, comprising:

a pair of goggles;

the goggles further comprising a main housing having a front side and a rear side, a view chamber comprising a face connecting section and a viewing lens; wherein, the face connecting section is connected on the rear side of the main housing;

an external air supply device for supplying forced air;

an air inlet connector is directly connected to and feeds air into a primary air duct; the air inlet connector comprising a ninety degree curve, and wherein the air inlet connector receives high pressure and high volume of air supplied from the external air supply device;

the primary air duct is connected in an off center position at an upper portion of the front side of the main housing;

an internal air port is positioned within the primary air duct, and further comprises left and right passage ways which forces the air to split equally to downward left and right directions, forcing the air to travel in a diametrically opposed manner across an outer surface of the viewing lens before traveling through a tapered air outlet having progressively narrowing curved air passages toward the center of the view chamber;

the tapered air outlet having a restriction rim located at a forward opening, forcing the forced air to travel outward to prevent any foreign particles from landing on the outer surface of the viewing lens; and further comprising a defogger on an interior portion of the view chamber, the defogger comprising an air charged vent strip located at an upper portion of the face connecting section; and an air outlet vent strip located at a bottom portion of the face connecting section; wherein, the primary air duct delivers a small portion of high pressure air directly to a full width of the air charged vent strip, and the air is directed downward upon the inside of the view chamber where it exits through the air outlet vent strip.

* * * * *